(12) United States Patent
Heyen et al.

(10) Patent No.: US 11,078,501 B2
(45) Date of Patent: Aug. 3, 2021

(54) METHODS OF FERMENTING MIXTURES THAT INCLUDE DI- AND TRI-SACCHARIDES FORMED AT LOW TEMPERATURE USING A MALTOPHILIC YEAST

(71) Applicant: Xylogenics, Inc., Indianapolis, IN (US)

(72) Inventors: Joshua W. Heyen, Brownsburg, IN (US); Mark G. Goebl, Indianapolis, IN (US); Kathryn A. Houin, Lebanon, IN (US); Matthew S. Kelker, Zionsville, IN (US); Nadaraj Palaniappan, Carmel, IN (US)

(73) Assignee: Xylogenics, Inc., Indianapolis, IN (US)

(*) Notice: Subject to any disclaimer, the term of this patent is extended or adjusted under 35 U.S.C. 154(b) by 0 days.

(21) Appl. No.: 16/235,119

(22) Filed: Dec. 28, 2018

(65) Prior Publication Data

US 2019/0203233 A1 Jul. 4, 2019

Related U.S. Application Data

(60) Provisional application No. 62/611,989, filed on Dec. 29, 2017.

(51) Int. Cl.
*C12P 7/06* (2006.01)
(52) U.S. Cl.
CPC ..................................... *C12P 7/06* (2013.01)
(58) Field of Classification Search
None
See application file for complete search history.

(56) References Cited

U.S. PATENT DOCUMENTS

2010/0151549 A1* 6/2010 Bhargava ............... C12P 19/14
435/161

OTHER PUBLICATIONS

Houghton-Larsen et al. Appl Environ Microbiol. Nov. 2006;72(11):7176-82. Epub Sep. 15, 2006. (Year: 2006).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession P32818. Oct. 1, 1993 (Year: 1993).*
Klosowski et al. J Biosci Bioeng. May 2010;109(5):466-71. Epub Nov. 22, 2009. (Year: 2009).*
Fatoni et al. Songklanakarin J. Sci. Technol. 34 (5), 525-531, Sep.-Oct. 2012 (Year: 2012).*

* cited by examiner

*Primary Examiner* — Christian L Fronda
(74) *Attorney, Agent, or Firm* — Faegre Drinker Biddle & Reath LLP

(57) ABSTRACT

Disclosed herein are materials and methods for the production of high concentrations of ethanol from plant starch material broken down into disaccharide and trisaccharide sugars such as maltose, isomaltose, and maltotriose from uncooked starch. Herein is also described use of a yeast strain capable of fermenting high maltose syrups into ethanol without the need to convert disaccharides or trisaccharides into glucose using exogenous glucoamylases.

13 Claims, 7 Drawing Sheets

METHODS OF FERMENTING MIXTURES THAT INCLUDE DI- AND TRI-SACCHARIDES FORMED AT LOW TEMPERATURE USING A MALTOPHILIC YEAST

CROSS-REFERENCE TO RELATED APPLICATION

This application claims the benefit under Title 35, U.S.C. § 119(e) of U.S. Provisional Patent Application Ser. No. 62/611,989, entitled PRODUCTION OF ETHANOL FROM MIXTURES THAT INCLUDE DI- AND TRI-SACCHARIDES FORMED AT LOW TEMPERATURES and filed on Dec. 29, 2017, the entire disclosure of which is hereby expressly incorporated by reference herein.

FIELD OF THE INVENTION

This invention relates generally to methods for producing high levels of ethanol by fermenting plant starches without the need for the addition of high levels of exogenous glucoamylases.

BACKGROUND AND SUMMARY

Numerous commercial methods exist to convert plant starch into substantial quantities of ethanol. However, these processes require considerable energy, as well as specialized enzymes to achieve maximum ethanol production. A need exists to improve these processes by reducing energy and enzyme costs. The invention described herein reduces the amount of heat required to liquefy plant starch, changes the enzymes to alter the sugar profile of the hydrolysed starch, and describes the use of yeast strains designed to utilize the altered sugar profile, resulting in more efficient fermentations and increased ethanol yield.

Some aspects of the present invention relate to methods for producing high levels of ethanol during fermentation of plant starches using a unique suite of maltose producing enzymes and maltophilic yeast strains capable of fermenting high maltose syrups into ethanol without the need to convert disaccharides and trisaccharides into glucose by the addition of exogenous glucoamylases. One maltophilic yeast stain that can be used to practice various embodiment of the present invention is described in Bailey, R. B. and Woodward, A. 1984, Isolation and characterization of a pleiotropic glucose repression resistant mutant of *Saccharomyces cerevisiae. Mol. Gen. Genet.* 193: 507-512.

In one embodiment, the present invention relates to a process whereby ground corn is liquefied using an alpha-amylase at concentrations between 0.5 and 4% and at temperatures less than about 70° C., preferably between about 28° C. to about 70° C. The syrup is then subjected simultaneously to an additional dose of maltogenic alpha-amylase, a pullulanase enzyme, and maltophilic yeast.

In one embodiment, the present invention relates to a process whereby ground corn is liquefied using an alpha amylase at concentrations between 0.5 and 4% and at temperatures less than about 70° C., preferably between about 28° C. and about 70° C. The syrup is then subjected simultaneously to a dose of beta-amylase, a pullulanase enzyme, and maltophilic yeast.

In one embodiment, the present invention relates to a process whereby ground corn is liquefied using an alpha-amylase followed by the addition of a different maltogenic alpha-amylase and a pullulanase, along with maltophilic yeast.

A first embodiment, is method for producing ethanol from plant matter, comprising the steps of: contacting a slurry of plant matter with: a first portion of an alpha-amylase; a portion of a maltophilic strain of *Saccharomyces*; and a portion of a beta amylase and/or a portion of a maltogenic alpha amylase at a temperature of 70° C. or less.

A second embodiment includes the method according to the first embodiment, further including the step of adding a portion of a pullulanase to the slurry.

A third embodiment includes the methods according to the first and second embodiments further including the step of adding a second portion of an alpha amylase to the slurry after the addition of the portion of maltophilic strain of *Saccharomyces*.

A fourth embodiment includes the methods according to the first through the third embodiments carried out in the absence of exogenous glucoamylases.

A fifth embodiment includes the methods of the first through the fourth embodiments, wherein the slurry is contacted with the first portion of alpha amylase at a temperature of about 50° C. to about 70° C., before the slurry is cooled to a temperature of about 31° C. or less and then contacted with the second portion of alpha amylase, the beta amylase and/or a portion of a maltogenic alpha amylase, and the maltophilic strain of *Saccharomyces*.

A sixth embodiment includes the method of the fifth embodiment, wherein the syrup is adjusted to a temperature of less than about 30° C. before the maltophilic strain of *Saccharomyces* is contacted with the syrup.

A seventh embodiment includes the methods of the first through the sixth embodiments, wherein the slurry of plant matter, comprises a portion of solids corn mash having a corn solids content of between about 28 weight percent (wt. %) to about 36 wt. % corn solids.

An eighth embodiment includes the methods of the first through the seventh embodiments practiced over a temperature range of about 28° C. to about 70° C.

A ninth embodiment includes the methods of the first through the eighth embodiments wherein the content of alpha amylases in the method is between about 0.5 wt. % to about 4 wt. %.

A tenth embodiment includes the methods of the first through the eighth embodiments wherein the content of alpha amylases in the method is between about 2.0 wt. % to about 4 wt. %.

An eleventh embodiment includes the methods of the first through the tenth embodiments wherein the content of beta amylases in the method is between about 0.5 wt. % to about 4 wt. %.

A twelfth embodiment includes the methods of the first through the tenth embodiments, wherein the content of beta amylases in the method is between about 2.0 wt. % to about 4 wt. %.

A thirteenth embodiment includes the methods of the first through the twelfth embodiments, wherein the content of pullulanase in the method is between about 0.5 wt. % to about 4 wt. %.

A fourteenth embodiment includes the methods of the first through the twelfth embodiments, wherein the content of pullulanase in the method is between about 2.0 wt. % to about 4 wt. %.

DESCRIPTION

Figure 1A:
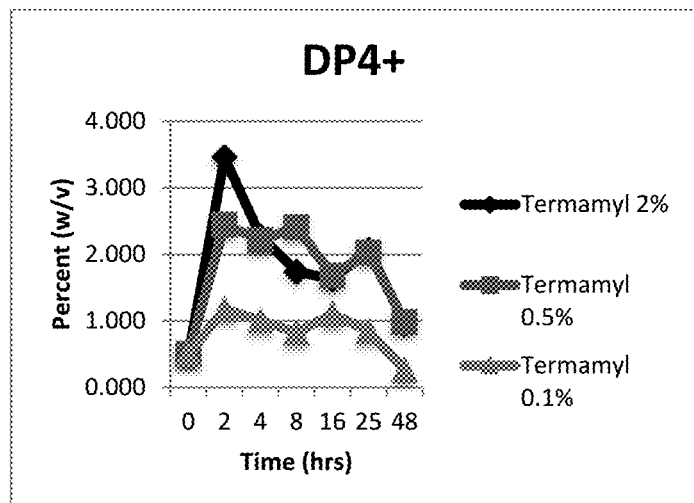
FIG. 1A. A graph illustrating the effect of dosages of an alpha-amylase on the production glucose from polysaccharides that includes more than 4 molecules of glucose (DP4+) production using one embodiment of the inventive process.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise, the term 'about' refers to a range of values plus or minus 10 percent, e.g. about 1.0 encompasses values from 0.9 to 1.1.

As used herein, the term 'maltophilic yeasts' refers to yeast strains with the ability to take up and metabolize maltose and glucose simultaneously, or almost simultaneously. Maltophilic yeast strains exhibit optimized maltose utilization capabilities, and reduced or no glucose repression.

In order to live and to reproduce all living things require energy. Plants produce energy and biomass through the process of photosynthesis, this requires leaves to harvest light energy and convert that energy into chemical energy (sugars). Like all seeds, when planted in soil, under the proper conditions a single kernel of corn will sprout to produce roots, stems, and leaves. This nascent corn plant may continue to grow over the course of a single growing season until it matures to produce clusters of its own kernels arranged on a cob. The nascent corn kernel as planted is devoid of characteristic plant parts such as leaves, root, a stem, etc., and therefore before it sprouts it cannot produce its own energy. For this reason, all seeds contain sufficient energy reserves to fuel root, stem, and leaf development. This chemical energy reserve in corn as in many plant seeds is starch.

A single kernel of domesticated corn typically comprises about 65-80% starch depending on the growing season and the specific corn variety. One form of starch, in its most basic form, is a polymer which includes many molecules of glucose linked through glycosidic bonds. This polymer commonly takes one or two basic forms either amylose or amylopectin.

Amylose is a primarily linear glucose polymer that can include on the order of up to 600 glucose molecules (600 degrees of polymerization, abbreviated as DP) linked together by α-(1,4) linkages. Another common form of starch found in corn is amylopectin; a large, highly branched glucose polymer that can range in degree of polymerization from hundreds of thousands to millions of glucose units. Glucose units in amylopectin are linked together by both α-(1,4) and α-(1,6) linkages, with the latter providing the branching structure. Together, many amylose and amylopectin molecules intertwine into an ordered superstructure known as a starch granule that looks much like a very small onion with concentric layers. A typical single kernel of domestic corn includes many starch granules comprising about 70-80% amylopectin and about 20-30% amylose.

Starch granules serve to store chemical energy for the seed in a very compact and recalcitrant state. This allows for a large amount of energy to be packed into a small space while limiting the ability of microbes to access this energy source. In this form, the starch is unavailable to the cells of the seed, and must therefore be broken down by enzymes into smaller molecules (monosaccharide and disaccharide sugars, e.g., glucose and maltose) that can be used by cells in the seed. The initial steps in producing fuel ethanol from corn feed stocks are designed to achieve the same goal: the breakdown of corn starch into usable energy. However, instead of fuelling cellular processes, the starch is instead prepared for fermentation into ethanol by organisms such as yeast.

The process to extract and hydrolyze corn starch in preparation for yeast fermentation starts when corn is received at the ethanol production facility. Corn shipments are evaluated for their suitability for use in ethanol production by measuring a variety of characteristics such as; starch content, protein content, amylose to amylopectin ratio, and other factors that can affect fermentation yield, such as moisture content, percentages of foreign particles, toxicity, and the like. These characteristics vary by region, corn hybrid, weather, farm practices, and other variables. It is therefore common to observe drastic swings in ethanol plant productivity from corn harvest to corn harvest. While each facility has its own standards, corn with low moisture content (≤20%), minimal foreign particles, and low toxicity provides for the most efficient and highest yielding fermentations and is generally regarded as the most valuable grade of corn.

Once corn has been received at the fermentation facility it is either stored on site or fed directly to a mill. In order to begin the process of extracting the corn starch, corn is first milled to a fine flour, using any number of milling technologies. Predominately two different milling procedures are utilized commercially in the United States: wet milling or dry milling. It is estimated that over 70% of the 13.3 billion gallons of fuel ethanol made in the United States in 2012 were made using the dry milling or dry grinding processes. For this reason, we focus on dry milling, although it should be understood that any other milling process can be used to practice various embodiments of the present invention.

The most common mill utilized in commercial ethanol production is a hammer mill. A typical hammer mill disrupts and grinds the corn kernel using sharpened shafts (hammers) spinning at high speed around a central axis. As the hammers spin, they grind corn entering the mill until the corn is ground small enough to pass through a screen of a given size. Screen size dictates the particle size of the flour and the particle size of the flour influences many downstream processes. Generally, as flour particle size increases, the downstream enzymatic hydrolysis of the starch becomes less efficient, ultimately decreasing the amount of sugar available to the yeast to ferment; thereby limiting the amount of ethanol produced in a given fermentation. While smaller particles may be preferred, producing flour with a small particle size requires more work (energy) as the hammer mill must operate at a higher amperage (or for a longer time) to produce ever smaller particles. Smaller particle sizes may also increase soluble solids in thin stillage, reducing centrifuge and evaporator efficiency during co-product feed production. Milling practices vary across ethanol production facilities, but on average flours having screen sizes between 2.5 and 3 mm are utilized commercially.

The next step, in the most commonly used commercial procedures, is mixing the ground corn flour with water at a certain ratio in a slurry mixer. The ratio of water to corn flour slurry determines the levels of solids in the final fermentation mash. Accordingly, the solids level is an extremely important parameter in fuel ethanol production. The solids level ultimately determines the amount of sugar that is available for fermentation by the yeast, and therefore it helps to determine the maximum ethanol level that can be achieved in the fermentation. Modern ethanol producers typically favour a 32% corn flour mixture (32% solids) but solid levels can vary from about 28% to about 34%, depending on facility and season. Fermentations carried out at this solid level are known as VHG fermentations (Very High Gravity). The ability to carry out VHG fermentations dramatically increases the efficiency of fuel ethanol production, but is currently limited to the aforementioned solid levels for a number of reasons.

Next, the corn flour and water slurry is mixed with an alpha-amylase enzyme in a slurry mixer. The enzyme/corn/water mixture (mash) is then pumped to a slurry tank where it is heated to about 90° C. to gelatinize the starch for hydrolysis by the alpha-amylase. Alpha-amylase is an endoenzyme, and thus hydrolyzes glycosidic bonds within the starch granule. The action of this enzyme quickly reduces the viscosity of the mash as it de-polymerizes the starch polymer into shorter chain dextrins. Commonly, the mash is held in the slurry tank for about 20 minutes and is then sterilized, further gelatinized, and sheared in a jet cooker at about 200° C. Jet cooked mash is then pumped into the liquefaction tanks, treated with a second dose of alpha-amylase, and held at 80° C.-90° C. for two hours to further break down the starch into dextrins. The mash is then cooled to 30° C.-34° C. and pumped into a fermentation tank along with yeast, nutrients, and a second enzyme (glucoamylase), to start a process known as SSF. Glucoamylase is an exo-acting beta-amylase that liberates glucose from the non-reducing ends of starch polymers and dextrins. In this method, glucoamylase 'spoonfeeds' fermentable sugars to the yeast for fermentation into ethanol. As outlined above, the upstream processing required to produce fermentable sugars from starch for yeast fermentation is both time and energy intensive.

The most commonly used glucoamylase enzyme technologies are designed to produce glucose from corn starch at a rate coinciding with the rate at which yeast ferments glucose, as glucose is preferentially metabolized by most yeast strains in commercial use. This is done in part because of a phenomenon known as glucose repression. Glucose repression is a prevalent feature of most strains of *Saccharomyces* yeast, in which glucose is metabolized to the exclusion of most other sugars, including maltose, isomaltose and maltotriose. Conventionally used strains of *Saccharomyces* will generally metabolize only, or at least predominately, glucose until the fermentation medium is completely (or almost completely) devoid of glucose. Accordingly, even in the presence of high concentrations of other fermentable sugars currently used yeast strains will not ferment other sugars to any appreciable degree until almost all of the glucose is consumed. The coordination of starch breakdown with glucose consumption by yeast is also necessitated in order to reduce osmolality of the fermentation environment. Currently used strains of yeast are sensitive to high osmotic pressure and a given concentration of glucose increases osmotic pressure about twice as much as similar levels of other sugars such as maltose. Moreover, most forms of glucoamylase enzymes currently used commercially are inhibited to various degrees by the presence of maltose which is almost always produced to some degree during the breakdown of starch.

For at least the reasons already cited, high quantities of glucose accumulation may lead to stuck fermentations and tremendous yield reduction. Accordingly, conventional fermentation systems have been developed to optimize glucose production from corn starch using glucoamylases to prepare media for fermentation by yeast, and to limit the rate of starch breakdown to coincide with the rate of yeast glucose fermentation. This limitation reduces the amount of starch that can be broken down and fermented in a given 54 hour fermentation; thus limiting maximum fermenter yield. As noted above, maltose, which is also a fermentable sugar produced from corn starch, is half as osmotically stressful to yeast and thus can accumulate to concentrations that are twice the acceptable glucose concentration in a fermenter. Therefore, the rate of starch breakdown can be greatly accelerated when producing maltose instead of glucose. Maltose production allows for higher solid levels to be loaded into a fermenter leading to higher ethanol levels, lower water usage, lower heat usage, and greater margins.

However, maltose fermentation in yeast is repressed by conventionally used strains of *Saccharomyces* preference for glucose. Thus, when using conventional yeasts the efficiency of maltose fermentations is greatly inhibited by the accumulation of even small amounts of glucose in the fermenter. Accordingly, glucose repression as exhibited by most conventional strains of *S. cerevisiae* has prevented the utilization of high gravity maltose fermentations. Some aspects of the present invention incorporate a series of enzyme treatments which convert plant starch at low temperatures to syrups which are high in maltose, which are then fermented by maltophilic yeast strains. By using the proper combination of fermentation feed stocks high in maltose and maltophilic strains of yeast it is possible to reduce glucose repression and to streamline the fermentation process.

In one aspect of the invention, the plant material is converted to ethanol using a method in which an alpha amylase is added to a slurry of plant matter and water and incubated at a temperature range of between about 50° C. to about 70° C. in order to break down longer chain polysaccharides and heat-kill any bacteria. Following cooling, a second enzyme and yeast are added.

In another aspect of the invention all enzymes and yeast are added simultaneously to a slurry of plant matter and water to begin fermentation concurrent with enzymatic digestion of the starches in the slurry. This type of fermentation is carried out at temperatures below about 38° C., preferably about in some embodiments at temperatures below about 34° C.

EXPERIMENTAL

Materials and Methods

1. Identifying an Enzyme Treatment to Yield High-Maltose Syrup from Plant Starch at Temperatures Less than 70° C.

Figure 1B:
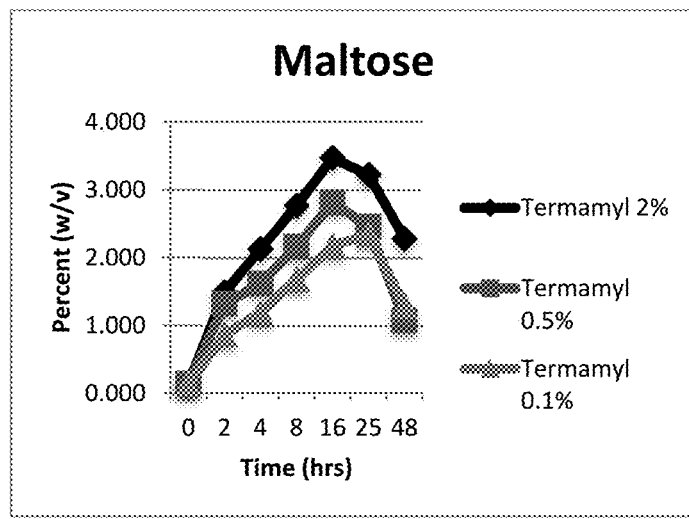
FIG. 1B. A graph illustrating the effect of dosages of an alpha-amylase on maltose production using one embodiment of the inventive process.
Figure 1C:
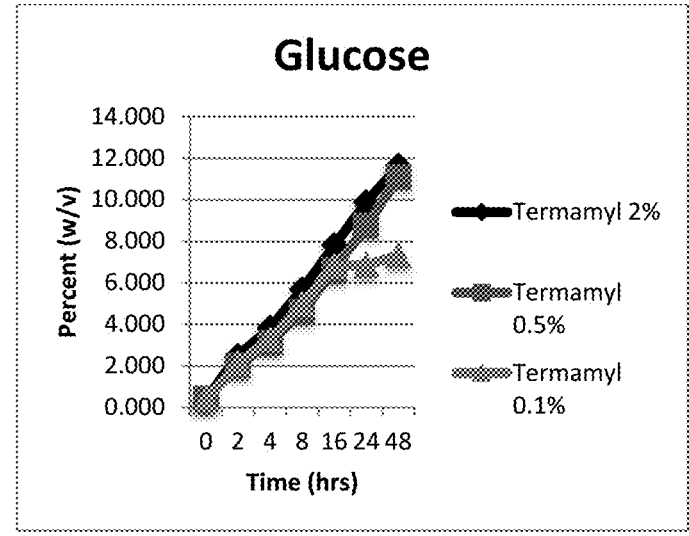
FIG. 1C. A graph illustrating the effect of dosages of an alpha-amylase on glucose production using one embodiment of the inventive process.
Figure 2A:
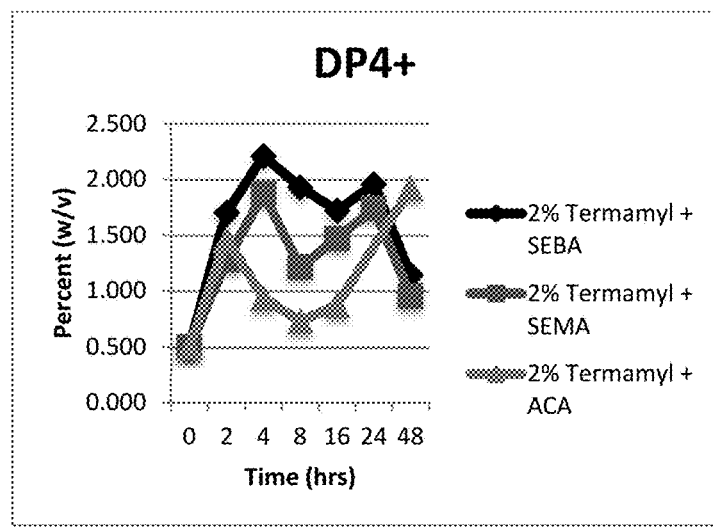
FIG. 2A. Graph of DP4+ levels produced at 60° C. using various combinations of maltogenic alpha- and beta-amylases.
Figure 2B:
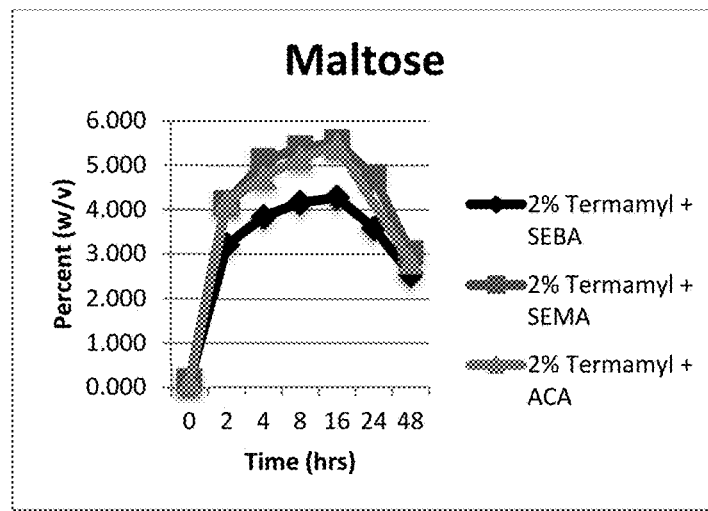
FIG. 2B. Graph of maltose levels produced at 60° C. using various combinations of maltogenic alpha- and beta-amylases.
Figure 2C:
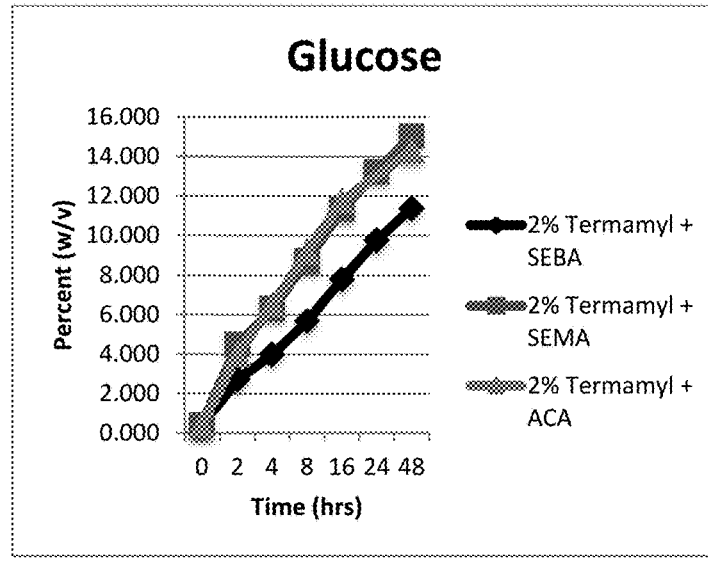
FIG. 2C. Graph of glucose levels produced at 60° C. using various combinations of maltogenic alpha- and beta-amylases.

The following experiments are used to determine optimal enzyme cocktails and conditions for producing high disaccharide/trisaccharide, low glucose syrups from corn starch under cold cook conditions. First, starch digestion by the alpha-amylase Termamyl L120 (produced by Novozymes, Franklinton, N.C., USA) was tested at different concentrations. Treating a 28% solid corn mash with 2% (w/w) Termamyl yields a preferable sugar mixture when compared to a 0.5% or 0.1% Termamyl treatment. This is due to increased DP4+ breakdown along with accumulating DP3 and maltose sugars, which reach 1.6 and 3.5% respectively after 16 hours. Final glucose levels (12%) were relatively high in Termamyl-only treatments (FIG. 1). Therefore, Termamyl was tested in combination with different maltogenic alpha-amylases and beta-amylases. A 28% corn mash with a 0.71 mm substrate grind size was treated with 2% Termamyl (w/w) and one of the following enzymes at 2% (w/w): SEBA (SEBStar BA; beta-amylase produced by Specialty Enzymes Chino, Calif., USA), SEMA (SEBStar MA; Maltogenic alpha-amylase produced by Specialty Enzymes), or ACA (ACA Concentrate, an alpha-amylase produced by Genencor-DuPont Cedar Rapids, Iowa, USA). The temperature during saccharification was maintained at about 50° C. The addition of SEBA, SEMA, or ACA to Termamyl increased maltose production and the maltose/glucose ratio. Glucose values for all enzyme treatments trended similarly, and were highest (11.5 to 14% w/v) after 48 hours. Maltose accumulates for the first 16 hours and then gradually declines. The Termamyl+SEBA and Termamyl+SEMA treatments are very similar in terms of DP4+ breakdown, and maltose and glucose production. The Termamyl+ACA treatment is not as effective at breaking down DP4+ and yields less maltose and glucose (FIG. 2).

Figure 3A:
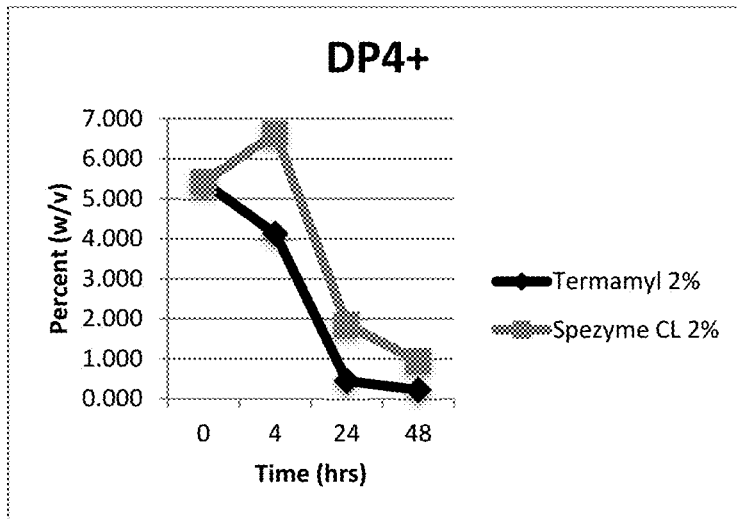
FIG. 3A. Graph comparing DP4+ levels produced from corn mash treated with two different alpha-amylases.
Figure 3B:
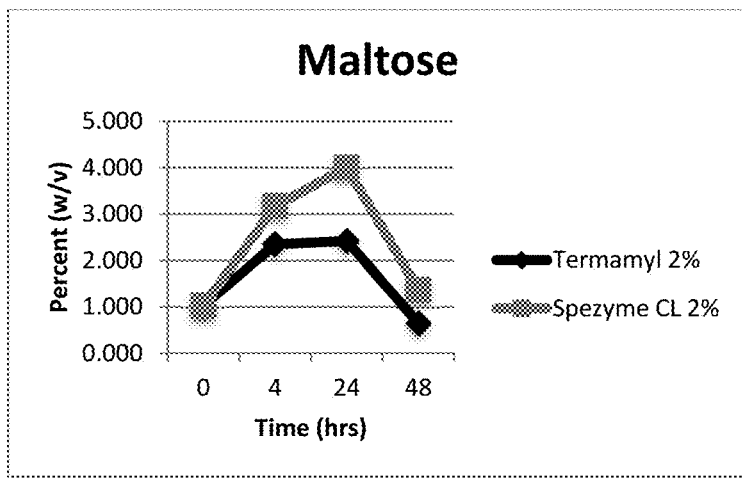
FIG. 3B. Graph comparing maltose levels produced from corn mash treated with two different alpha-amylases.
Figure 3C:
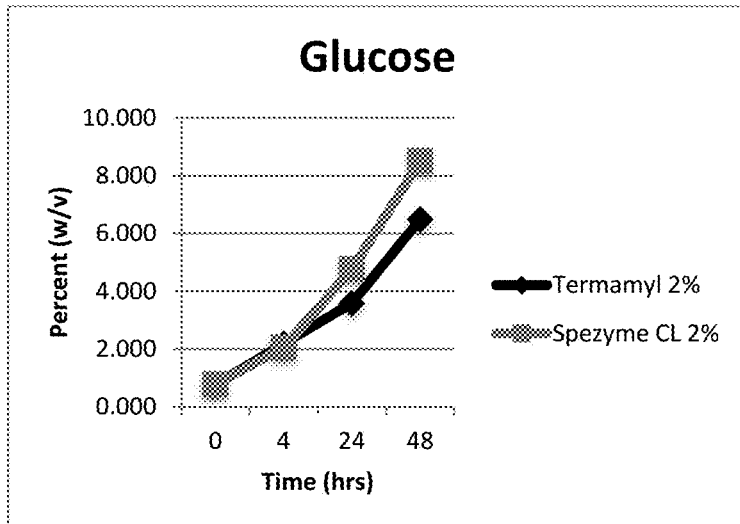
FIG. 3C. Graph comparing glucose levels produced from corn mash treated with two different alpha-amylases.
Figure 4A:
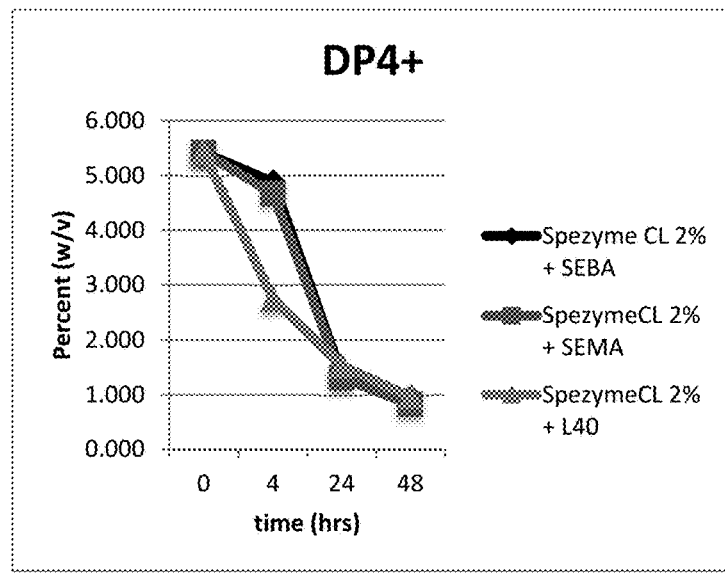
FIG. 4A. Graph of DP4+ profile produced at 60° C. using various combinations of maltogenic alpha- and beta-amylases.
Figure 4B:
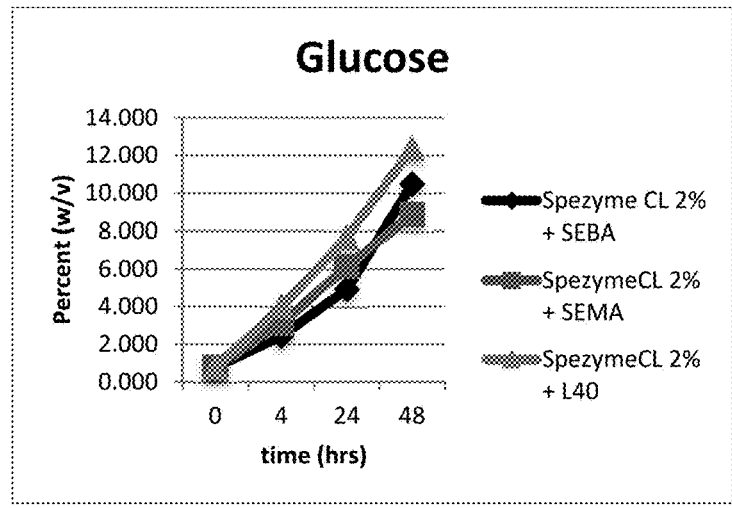
FIG. 4B. Graph of glucose profile produced at 60° C. using various combinations of maltogenic alpha- and beta-amylases.
Figure 4C:
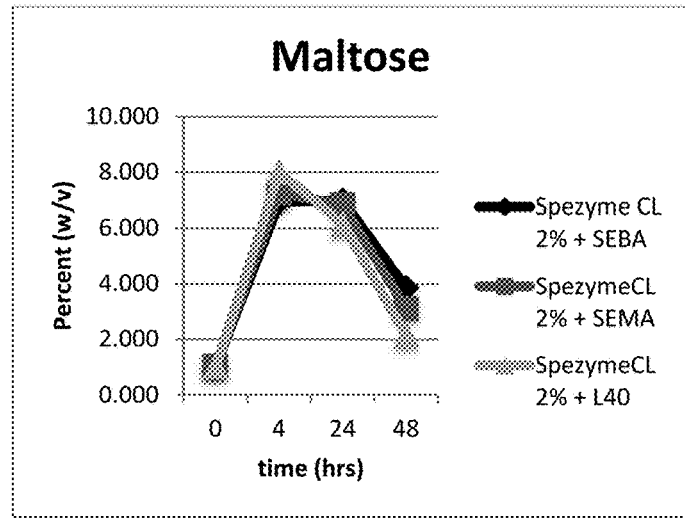
FIG. 4C. Graph of maltose profile produced at 60° C. using various combinations of maltogenic alpha- and beta-amylases.

Termamyl L120 was compared with Spezyme CL (alpha-amylase produced by Genencor-DuPont) at about 36° C. Spezyme CL is an effective alpha-amylase and produces more DP3, maltose and glucose than Termamyl L120 after 24 and 48 hours (FIG. 3). (DP3+Maltose): glucose ratios at 24 hours are higher in mash treated with Spezyme CL (1.29) than mash treated with Termamyl (0.95). Spezyme CL in combination with SEL40 (SEBStar L40; fungal alpha amylase by Specialty Enzymes) liberates more maltose and glucose than Spezyme CL alone; however, the (DP3+maltose): glucose ratio is lower for Spezyme CL+SEL40 when compared to Spezyme CL. Furthermore, Spezyme CL in combination with either SEBA or SEMA produces higher levels of DP3, maltose, and glucose than Spezyme CL alone. (DP3+maltose): glucose ratios are higher at all time points for these enzyme cocktails (FIG. 4).

2. Fermentation of Disaccharide and Trisaccharide Syrups with Maltophilic Yeasts.

Figure 5:
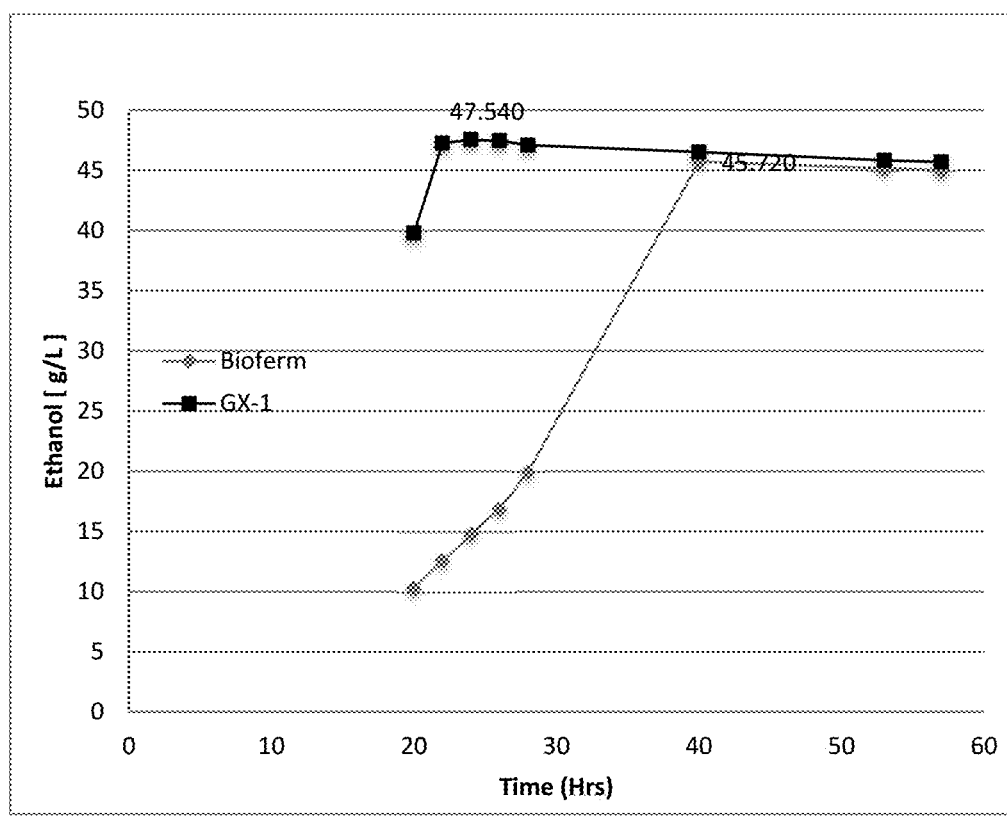
FIG. 5. Graph illustrating that maltophilic yeast strains consume high maltose syrups and produce ethanol more rapidly than non-maltophilic yeast strains.
Figure 6:
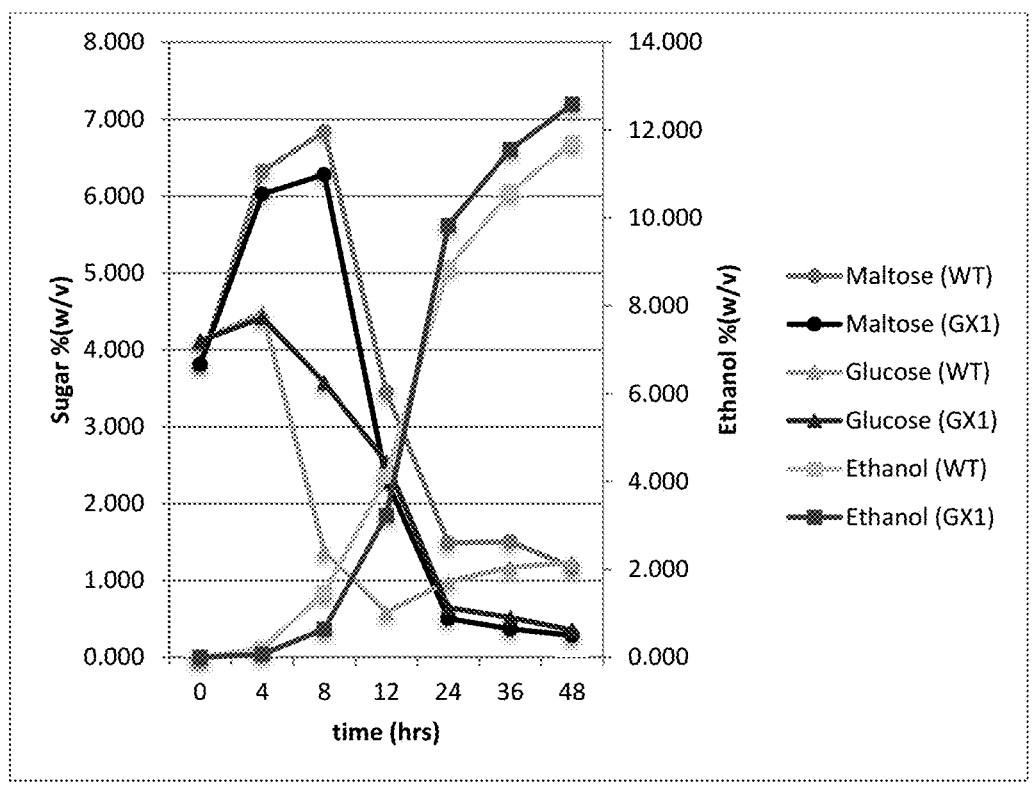
FIG. 6. Graph illustrating DP4+, maltose and glucose production and consumption, along with ethanol production for non-maltophilic and maltophilic yeast strains during SSF (Simultaneous Saccharification and Fermentation) using corn mash with 28% solids. The mash was treated at 60° C. using Termamyl 3% (w/w) for 4 hours prior to cooling then simultaneous addition of yeast and a beta amylase (SEBStar Beta amylase also known as SEBA at 2% w/w).

Maltophilic yeasts co-consume maltose and glucose and some strains may show a preference for maltose as compared to glucose. One strain of maltophilic yeast, referred to herein as GX1, consumes maltose much more rapidly than an isogenic non-maltophilic industrial yeast strain (FIG. 5). The GX1 strain is a GRR1 knock-out of Ethanol Red. In the present process, 3% (w/w) Termamyl L120 is incubated with a 28% corn mash for 4 hours at 60° C., the mash is then cooled to 34° C. and 2% (w/w) SEBA and the maltophilic yeast GX1 are added simultaneously. Simultaneous saccharification and fermentation is carried out at 34° C. for 48 hours. GX1 produces more ethanol than the isogenic non-maltophilic strain after 48 hours (FIG. 6). This increase in ethanol production may be due to an increase in the consumption of both maltose and glucose by the GX1 strain. Maltose levels were higher than glucose levels from hours 4-12 for GX1 fermentations, after which point low levels of both glucose and maltose were maintained for the remainder of the fermentation. The non-maltophilic strain quickly consumed available glucose, but maltose levels remained high. Only approximately 36 hours after the fermentation start do maltose levels drop to the level of glucose (FIG. 6). The slow utilization of maltose is likely due to the inherent glucose repression effects hindering maltose fermentation.

Figure 7A:
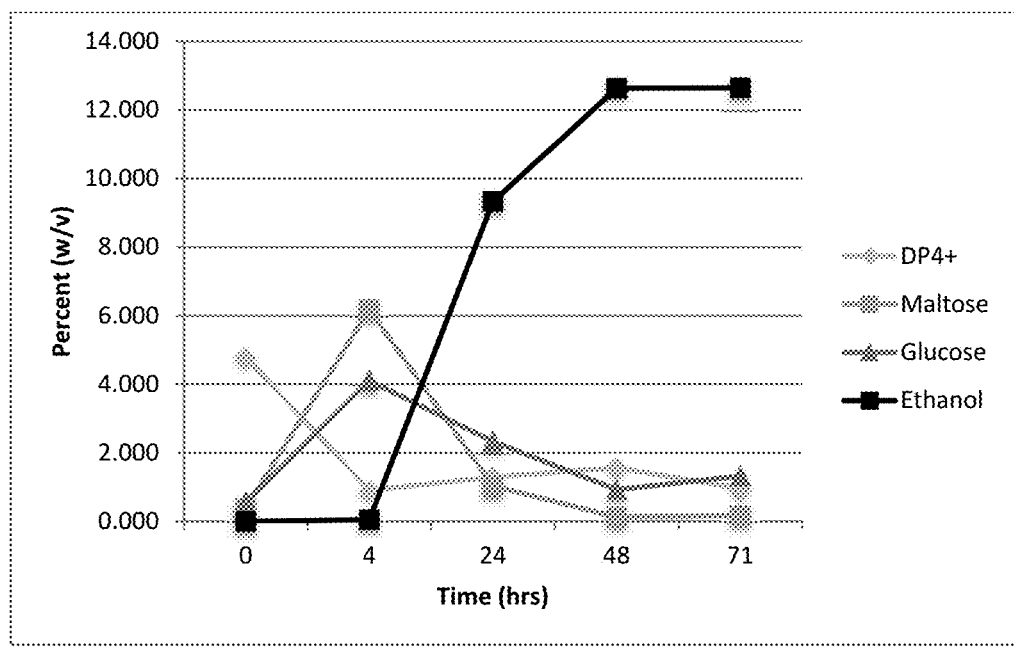
FIG. 7A. Graph illustrating data from a representative fermentation according to one embodiment of the invention showing DP4+, maltose, and glucose production and consumption, and ethanol production using a maltophilic yeast strain and the enzyme Termamyl.
Figure 7B:
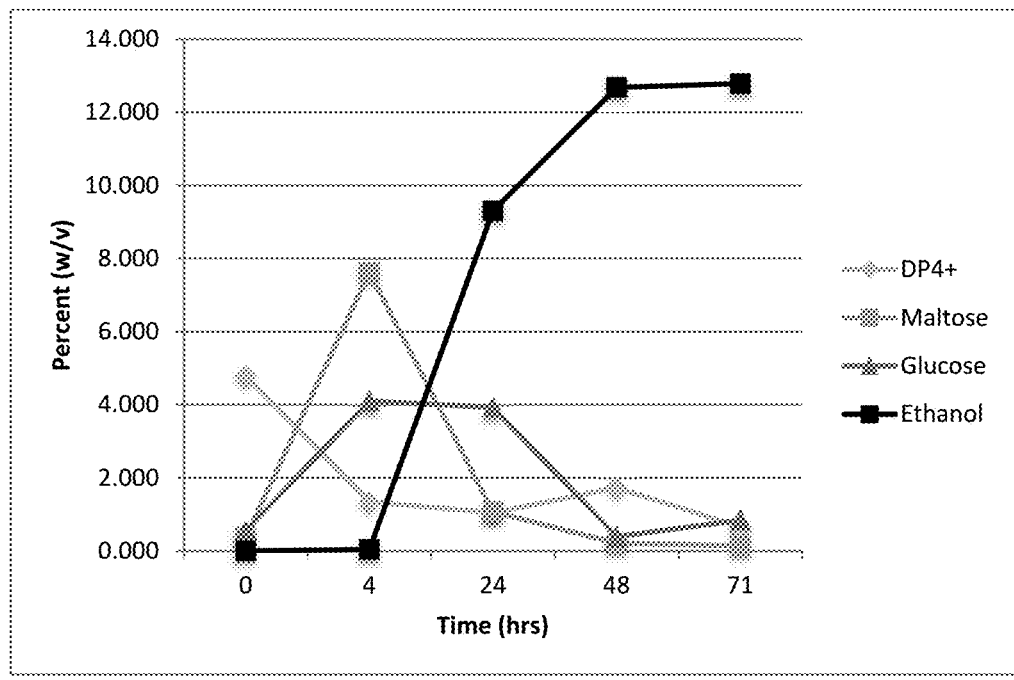
FIG. 7B. Graphs illustrating data from a representative fermentation according to one embodiment of the invention showing DP4+, maltose, and glucose production and consumption, and ethanol production using a maltophilic yeast strain and the enzyme Spezyme CL.

The process may be conducted without the need for a discrete digestion step. In a separate experiment, 28% solid corn mash is simultaneously digested with 2% Termamyl L120, 2% SEBStar L40, and 2% Optimax L-1000 (a pullulanase produced by DuPont), and fermented with GX1 yeast at 36° C. Such fermentations initially produce high maltose syrups and yield final ethanol levels equivalent to those of typical glucoamylase-based fermentations, whereby final ethanol values finish around 12.6% (w/v). Fermentations finish within 48 hours. Saccharification with 2% Spezyme CL, 2% SEBStar L40, and 2% Optimax L-1000 produces slightly higher maltose syrups and nearly equivalent final ethanol levels, and again finishes fermentation within 48 hours (FIG. 7).

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology is being illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method for producing ethanol from a plant matter, comprising the steps of:
   liquefying of grain solids by treating a combination of the grain solids and water with an alpha-amylase at a concentration between 0.5 to 4 wt. % of the grain solids at a temperature of 70° C. or lower to form a grain slurry;
   adding a maltogenic alpha-amylase; a maltophilic strain of *Saccharomyces*; and beta amylase to the grain slurry to form a mixture; and
   fermenting the mixture at a temperature of about 38° C. or lower,
wherein the maltophilic strain of *Saccharomyces* is a GRR1 knock-out of Ethanol Red.

2. The method according to claim 1, further including the step of adding a pullulanase to the mixture.

3. The method according to claim 1, further including the step of adding a second amount of an alpha amylase to the mixture during the fermentation step.

4. The method according to claim 1, wherein the method is carried out in the absence of exogenous glucoamylases.

5. The method according to claim 1, wherein the grain slurry is formed by treating a combination of the grain solids and water with an alpha-amylase at a concentration between 0.5 to 4 wt. % of the grain solids at a temperature in the range of about 50° C. to 70° C.

6. The method according to claim 5, wherein the grain slurry is adjusted to a temperature of less than about 30° C. before the maltophilic strain of *Saccharomyces* is contacted with the grain slurry.

7. The method according to claim 1, wherein the grain slurry of the plant matter comprises a portion of grain solids having grain solids content of between about 28 weight percent (wt. %) to about 36 (wt. %) grain solids.

8. The method according to claim 1, wherein the content of alpha amylases in the method is between about 2.0 wt. % grain solids to about 4 wt. % grain solids.

9. The method according to claim 1, wherein the content of beta amylases in the method is between about 0.5 wt. % grain solids to about 4 wt. % grain solids.

10. The method according to claim 9, wherein the content of beta amylases in the method is between about 2.0 wt. % grain solids to about 4 wt. % grain solids.

11. The method according to claim 2, wherein the content of pullulanase in the method is between about 0.5 wt. % grain solids to about 4 wt. %.

12. The method according to claim 11, wherein the content of pullulanase in the method is between about 2.0 wt. % grain solids to about 4 wt. % grain solids.

13. The method of claim 1, wherein the grain is corn.

* * * * *